US011491051B2

(12) United States Patent
Lu et al.

(10) Patent No.: US 11,491,051 B2
(45) Date of Patent: Nov. 8, 2022

(54) SHUNT FOR DRAINING OCULAR FLUID (71) Applicant: TAIWAN FIBER OPTICS, INC., Taipei (TW)

(72) Inventors: Luke Lu, San Diego, CA (US); Hsiao Sen Tseng, Taichung (TW); Michelle Lu, San Diego, CA (US); Emily Lu, San Diego, CA (US)

(73) Assignee: TAIWAN FIBER OPTICS, INC., Taipei (TW)

( * ) Notice: Subject to any disclaimer, the term of this patent is extended or adjusted under 35 U.S.C. 154(b) by 825 days.

(21) Appl. No.: 16/398,380

(22) Filed: Apr. 30, 2019

(65) Prior Publication Data

US 2020/0345549 A1    Nov. 5, 2020

(51) Int. Cl.
*A61F 9/007* (2006.01)
*A61L 31/02* (2006.01)
*A61L 31/04* (2006.01)
*A61L 31/14* (2006.01)

(52) U.S. Cl.
CPC ........ *A61F 9/00781* (2013.01); *A61L 31/026* (2013.01); *A61L 31/044* (2013.01); *A61L 31/148* (2013.01); *A61F 2210/0004* (2013.01); *A61F 2220/0008* (2013.01); *A61F 2230/0006* (2013.01); *A61F 2230/0008* (2013.01); *A61F 2230/0017* (2013.01); *A61F 2230/0067* (2013.01); *A61F 2230/0071* (2013.01)

(58) Field of Classification Search
CPC ................ A61F 9/0017; A61F 9/00781; A61F 2250/0013; A61F 2250/0069; A61F 2250/0067; A61F 2210/0004; A61F 2220/0008; A61F 2230/0006; A61F 2230/0008; A61F 2230/0017; A61F 2230/0067; A61F 2230/0071; A61K 9/0051; A61L 31/026; A61L 31/044; A61L 31/148; A61L 2430/16; A61L 31/128

See application file for complete search history.

(56) References Cited

U.S. PATENT DOCUMENTS

| 5,300,020 A * | 4/1994 | L'Esperance, Jr. ........................ A61F 9/00781 604/9 |
| 2003/0229303 A1* | 12/2003 | Haffner ............... A61F 9/00781 604/8 |
| 2007/0298075 A1* | 12/2007 | Borgia ................ A61M 31/002 424/428 |
| 2008/0161741 A1* | 7/2008 | Bene ................... A61F 9/00781 604/9 |
| 2010/0004635 A1* | 1/2010 | Lin ..................... A61F 9/00781 216/37 |
| 2012/0197217 A1* | 8/2012 | Coldren ............... A61F 9/0017 604/294 |
| 2016/0270958 A1* | 9/2016 | de Silva Curiel .. A61F 9/00781 |

* cited by examiner

*Primary Examiner* — Philip R Wiest
*Assistant Examiner* — Alessandro R Del Priore (57) ABSTRACT

A shunt for draining ocular fluid of one embodiment includes a tubular body formed of a mesh material including bioactive glass fiber and collagen, the tubular body including an implantation member and a conduit through the implantation member. The implantation member and the conduit are formed integrally. Other embodiments are also contemplated.

6 Claims, 10 Drawing Sheets

SHUNT FOR DRAINING OCULAR FLUID

BACKGROUND OF THE INVENTION

1. Field of the Invention

The invention relates to tube shunts and more particularly to a shunt having a tubular body attached to sclera for draining ocular fluid from the eye, thereby lowering ocular pressure.

2. Description of Related Art

For treating glaucoma, conventional shunts for draining ocular fluid are made of metal or polymer. The shunt may form a scab over a healed cut and the eye of a patient may feel a degree of discomfort due to heavy weight even if the shunt is small. Further, there is a concern of risk of metal and polymer staying in the human body after some years. It is always a long term concern of risk, as another surgery for removing the shunt is required. It is understood that there is risk in surgery.

Thus, the need for improvement of the shunt still exists.

SUMMARY OF THE INVENTION

It is therefore one object of the invention to provide a shunt for draining ocular fluid, comprising a tubular body formed of a mesh material including bioactive glass fibers and collagen, the tubular body including an implantation member and a conduit through the implantation member; wherein the implantation member and the conduit are formed integrally.

It is another object of the invention to provide a shunt for draining ocular fluid, comprising a tubular body formed of a bioactive glass material, the tubular body including an implantation member and a conduit; wherein the implantation member and the conduit are formed integrally; wherein the implantation member includes at least one anchor member; and wherein the conduit passes through the implantation member.

The invention has the following advantages and benefits in comparison with the conventional art:

By being constructed as indicated above, the tubular body can be attached to sclera so that ocular fluid may leave the eye to flow through the conduit, thereby lowering ocular pressure. Further, the tubular body is formed of a bioactive glass material, i.e., capable of being absorbed by the body tissues. Specifically, the tubular body is attracted to the body tissues and tends to be dissolved by the body tissues. Thus, a glaucoma patient may have a minimum feeling of discomfort when the tubular body is attached to the sclera. Furthermore, the tubular body may be absorbed by the body tissues as time goes by, thereby forming a tubular, flexible member for healing purposes.

The tubular body may be constructed as a double-layer member in which a first layer of the tubular body is formed of the bioactive glass material and a second layer thereof is formed of a bio-glass material. Specifically, the second layer is formed of a bioactive glass material having a high composition of silica or a bio-inert glass material. Thus, it is possible to control the strength of the tubular body and the time for the tubular body to be absorbed by the body tissues by adjusting weight percentages of compositions of the first and second layers.

The above and other objects, features and advantages of the invention will become apparent from the following detailed description taken with the accompanying drawings.

DETAILED DESCRIPTION OF THE INVENTION

Figure 1:
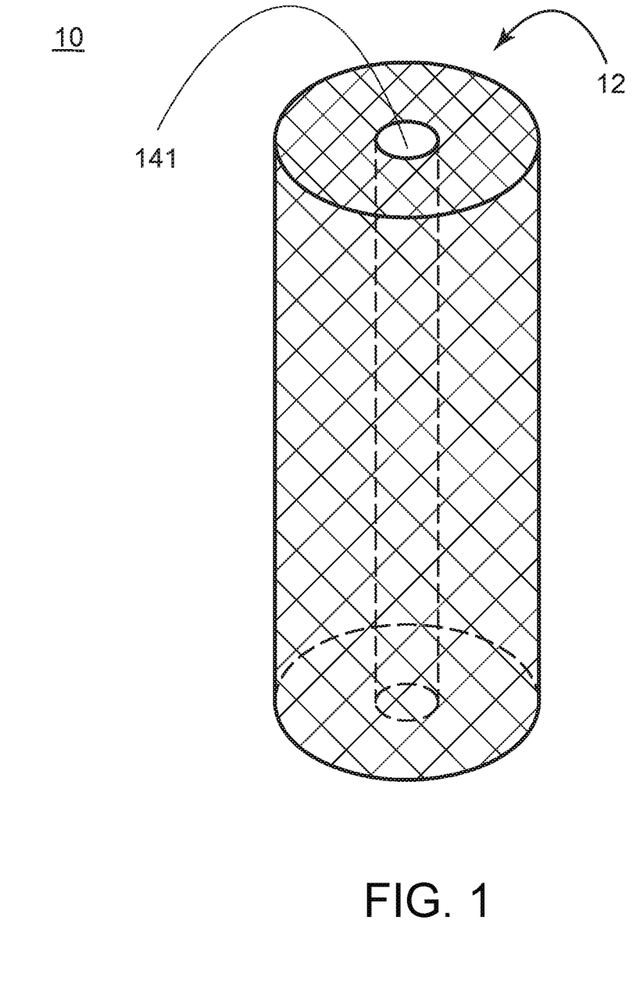
FIG. 1 is a perspective view of a shunt for draining ocular fluid according to a first preferred embodiment of the invention.

Referring to FIG. 1, a shunt for draining ocular fluid in accordance with a first preferred embodiment of the invention comprises a tubular body 10 formed of a mesh material including bioactive glass fiber and collagen. The tubular body 10 includes an implantation member 12 and a conduit 141 through the implantation member 12. The implantation member 12 and the conduit 141 are formed integrally. The dispersion capability of the tubular body 10 can be increased or decreased by different compositions of bioactive glass fibers, bioresorable fibers and collagen. The tubular body 10 allows ocular fluid in an anterior section of an eye to flow through in a controlled manner for lowering intraocular pressure. As shown, the tubular body 10 does not have a specific direction for implantation into the eye. Thus, the implantation member 12 can be disposed at either end of the tubular body 10.

Figure 2:
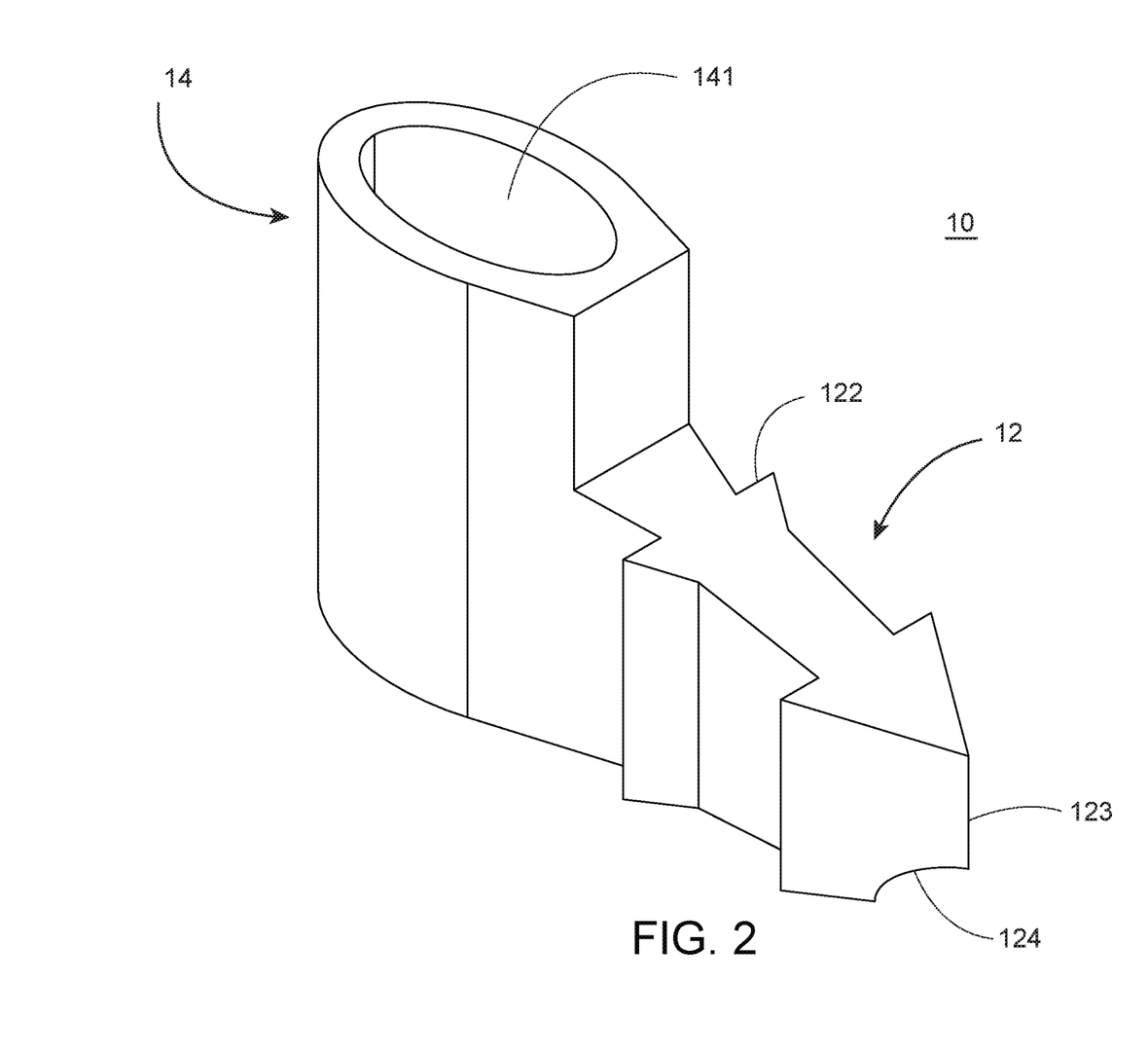
FIG. 2 is a perspective view of a shunt for draining ocular fluid according to a second preferred embodiment of the invention.
Figure 3:
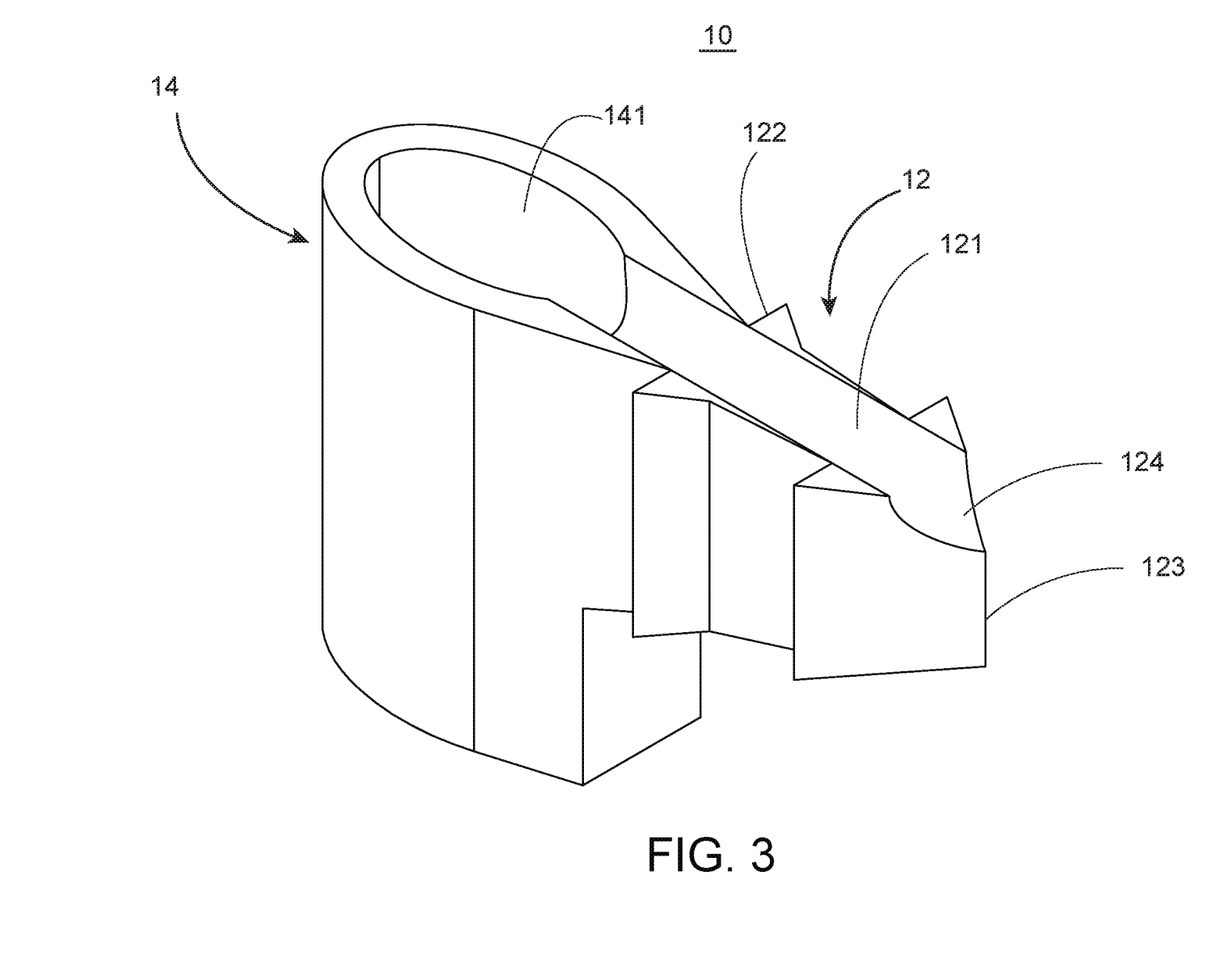
FIG. 3 is another perspective view of FIG. 2 showing bottom characteristics of the shunt (i.e., the tubular body)
Figure 4:
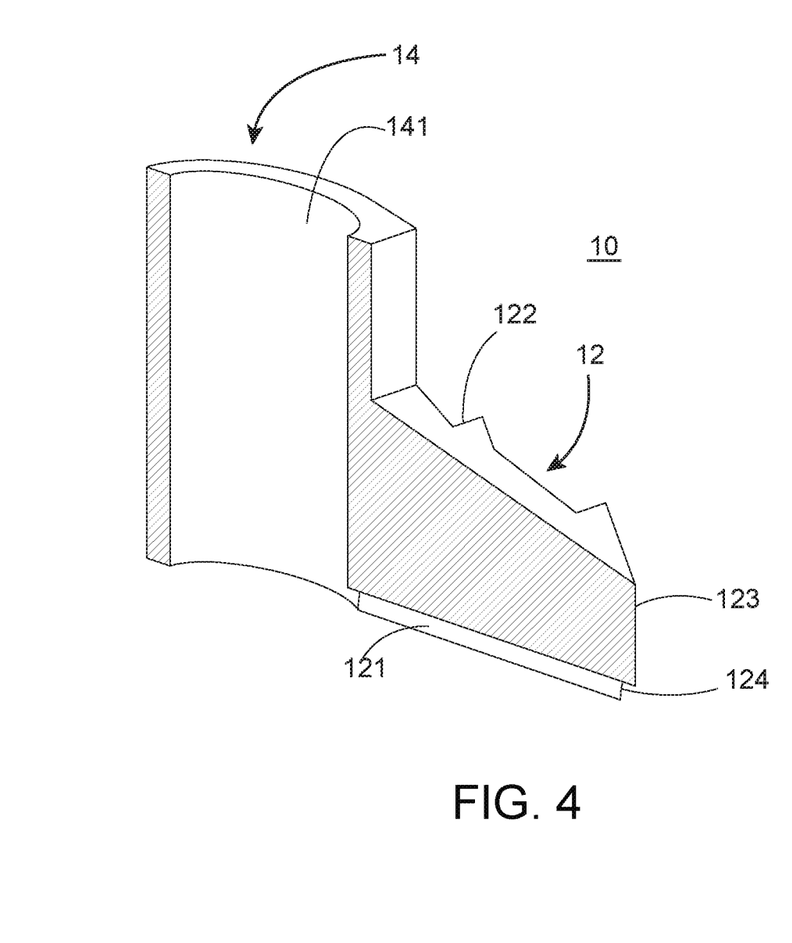
FIG. 4 is a longitudinal sectional view of the shunt shown in FIG. 2.

Referring to FIGS. 2 to 4, a shunt for draining ocular fluid in accordance with a second preferred embodiment of the invention comprises a tubular body 10 formed of a bioactive glass material. The tubular body 10 includes an implantation member 12 and a fluid guide member 14 extending out of the implantation member 12. A conduit 141 is disposed through the fluid guide member 14. The fluid guide member 14 is perpendicular to the implantation member 12 so that the tubular body 10 is shaped as an L in a longitudinal section. The implantation member 12 includes a sharp end 123, a cavity 124 on a lower portion of the sharp end 123, a plurality of sharp projections 122 on both sides of the implantation member 12, and a bottom channel 121 communicating with both the conduit 141 and the cavity 124. The conduit 141 has an oval opening at one end. It is noted that the opening may be shaped as a circle, a hexagon, or a polygon in other embodiments. The conduit 141 has a smooth surface and has an axial length of less than 0.5 mm and a diameter of less than 0.2 mm. By constructed as above, the tubular body 10 can be absorbed or be degraded in body tissues in several months to form a tubular, flexible member for healing purposes.

Figure 4A:
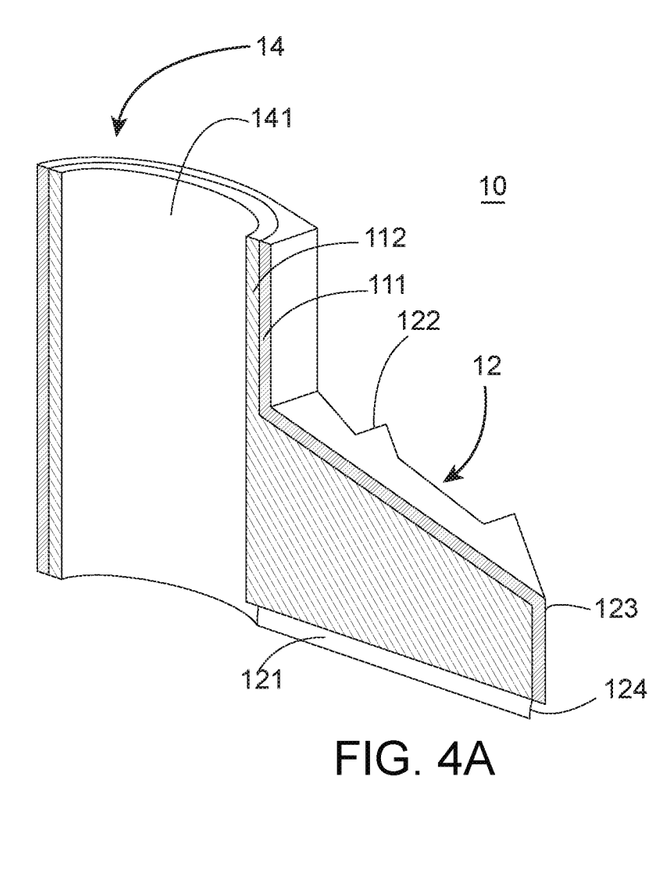
FIG. 4A is a view similar to FIG. 4 showing a double-layer configuration of the shunt.

Referring to FIG. 4A, the tubular body 10 of the second preferred embodiment is constructed as a double-layer member in which a first layer 111 of the tubular body 10 is formed of the bioactive glass material and a second layer 112 thereof is formed of a bio-glass material. It may take several months for the second layer 112 to be absorbed or to be degraded in the body tissues if it is formed of a bioactive glass material having a high composition of silica. Alternatively, the second layer 112 is formed of a bio-inert glass material and the second layer 112 is not subject to be absorbed or to be degraded, i.e., remained in the body tissues forever.

Figure 5:
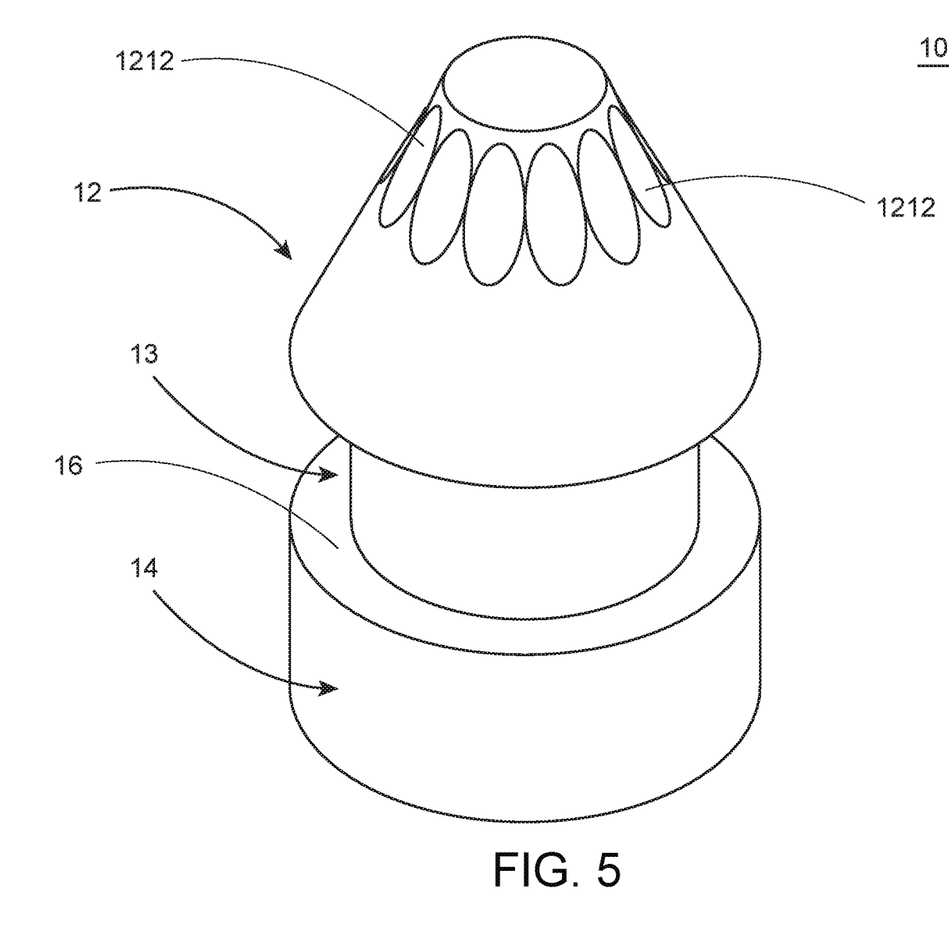
FIG. 5 is a perspective view of a shunt for draining ocular fluid according to a third preferred embodiment of the invention.
Figure 6:
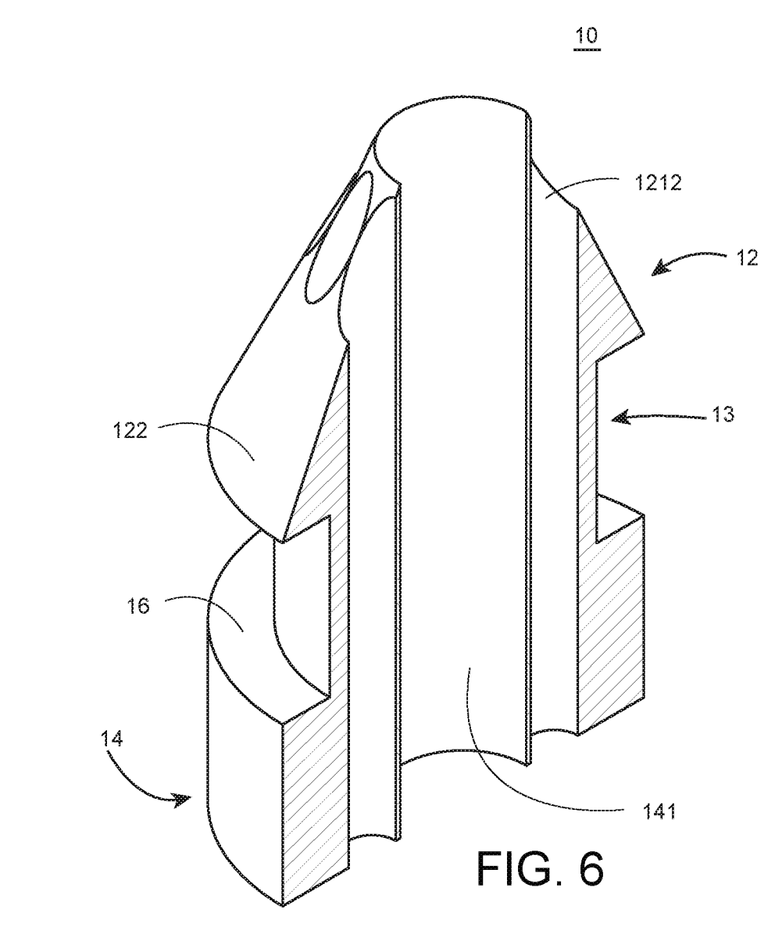
FIG. 6 is a longitudinal sectional view of the shunt shown in FIG. 5.

Referring to FIGS. 5 and 6, a shunt for draining ocular fluid in accordance with a third preferred embodiment of the invention comprises a tubular body 10 formed of a bioactive glass material. The tubular body 10 includes an implantation member 12 and a fluid guide member 14 extending out of the implantation member 12. A conduit 141 is disposed through the fluid guide member 14. The fluid guide member 14 is aligned with the implantation member 12 so that the tubular body 10 is shaped as an I in a side elevation. The implantation member 12 includes a tapered anchor member 122 at one end, a plurality of lengthwise tunnels 1212 equally spaced around and separated from the conduit 141, each tunnel 1212 being parallel to the conduit 141 and passing through the tubular body 10 to have two ends open, an annular groove 13 disposed between the tapered anchor member 122 and the fluid guide member 14, and an annular shoulder 16 disposed between the annular groove 13 and the fluid guide member 14. The conduit 141 has a circular opening at one end. It is noted that the opening may be shaped as an oval, a hexagon, or a polygon in other embodiments.

Figure 6A:
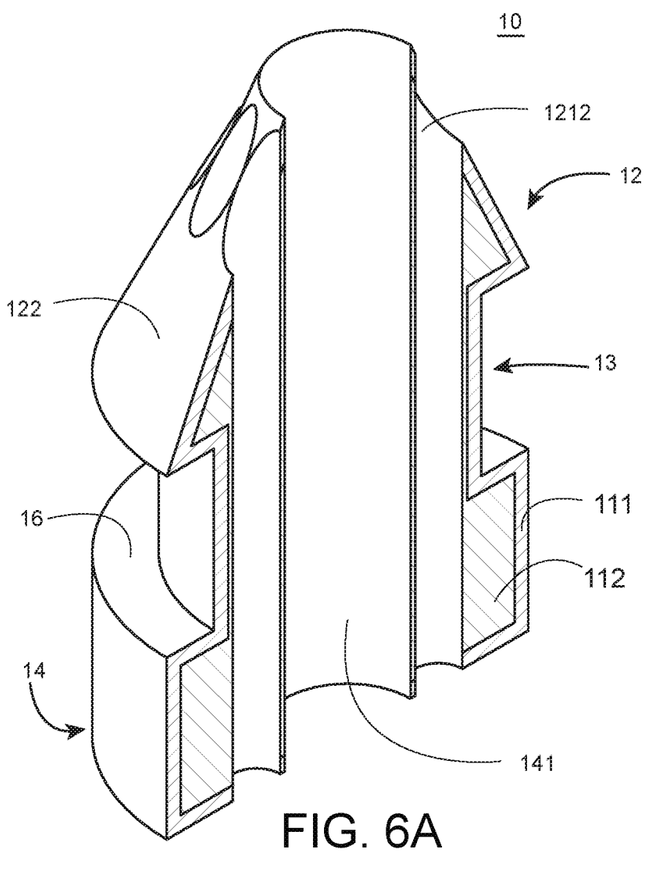
FIG. 6A is a view similar to FIG. 6 showing a double-layer configuration of the shunt.

Referring to FIG. 6A, the tubular body 10 of the third preferred embodiment is constructed as a double-layer member in which a first layer 111 of the tubular body 10 is formed of the bioactive glass material and an second layer 112 thereof is formed of a bio-glass material. The second layer 112 may be formed of a bioactive glass material having a high composition of silica or a bio-inert glass material. It may take several years for the second layer 112 to be absorbed or to be degraded in the body tissues if it is formed of a bioactive glass material having a high composition of silica. Alternatively, the second layer 112 is formed of a bio-inert glass material and the second layer 112 is not subject to be absorbed or to be degraded, i.e., remained in the body tissues forever.

Figure 7:
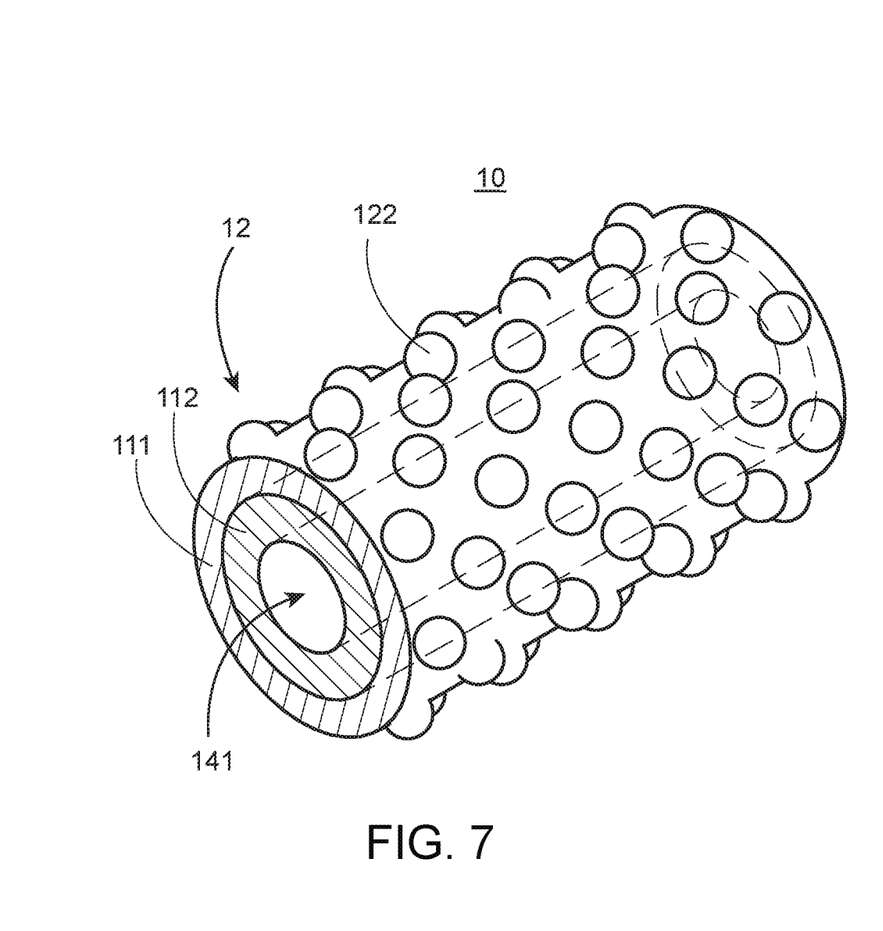
FIG. 7 is a perspective view of a shunt for draining ocular fluid according to a fourth preferred embodiment of the invention.
Figure 7A:
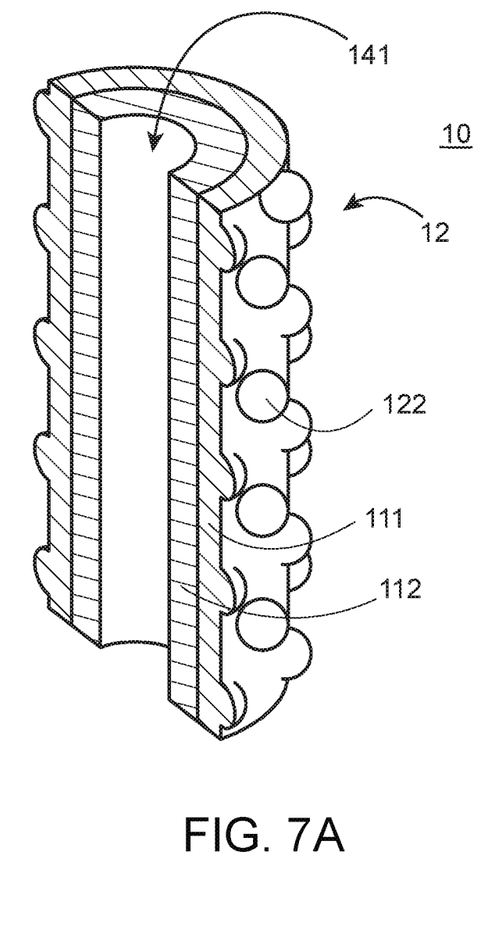
FIG. 7A is a longitudinal sectional view of the shunt shown in FIG. 7.

Referring to FIGS. 7 and 7A, a shunt for draining ocular fluid in accordance with a fourth preferred embodiment of the invention comprises a tubular body 10 including a first layer 111 formed of a bioactive glass material and a second layer 112 formed of a bio-glass material. The second layer 112 and the first layer 111 are fused by fusion process. Specifically, the second layer 112 is formed of a bioactive glass material having a high composition of silica or a bio-inert glass material. It may take several months for the second layer 112 to absorb or degrade in the body tissues if it is formed of a bioactive glass material having a high composition of silica. Alternatively, the second layer 112 is formed of a bio-inert glass material and the second layer 112 is not subject to degradation, i.e., remained in the body tissues forever.

A tubular implantation member 12 is comprised of the second layer 112 and the first layer 111 and includes a plurality of substantially half-spherical protrusions 122 on an outer surface for adhering purposes. A conduit 141 is integrally formed with and passes through the implantation member 12 to have two ends open.

Figure 8:
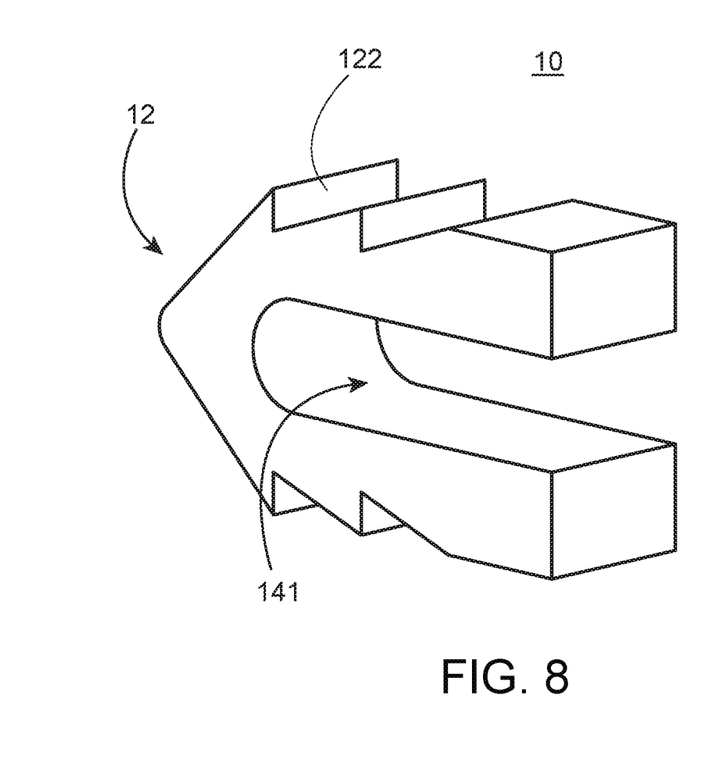
FIG. 8 is a perspective view of a shunt for draining ocular fluid according to a fifth preferred embodiment of the invention.
Figure 8A:
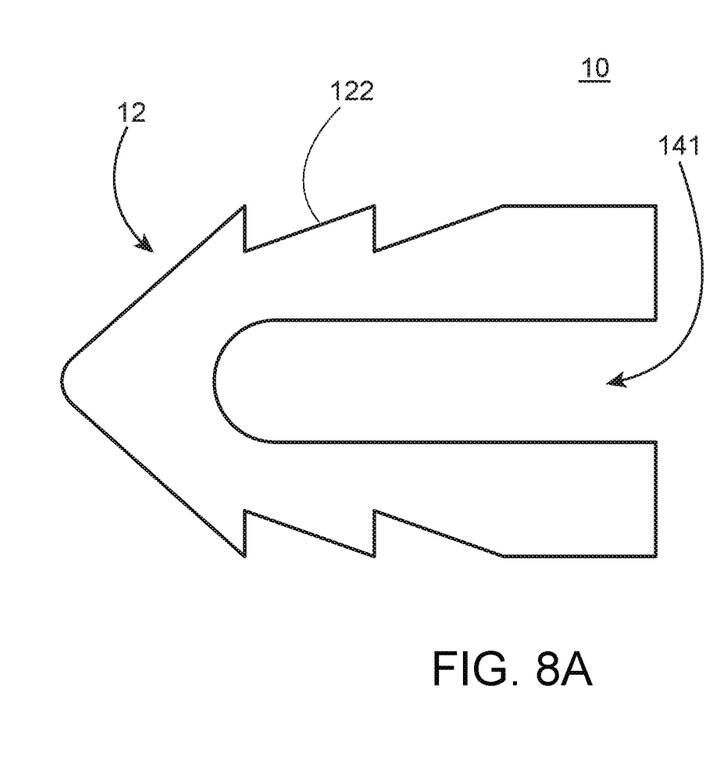
FIG. 8A is a side elevation of FIG. 8.

Referring to FIGS. 8 and 8A, a shunt for draining ocular fluid in accordance with a fifth preferred embodiment of the invention comprises a tubular body 10 including an implantation member 12 and a conduit 141 integrally formed with the implantation member 12. The implantation member 12 includes a plurality of sharp projections 122 on both sides. The conduit 141 is in the implantation member 12 and has one end and two sides open. The tubular body 10 is formed of a bioactive glass material. Thus the tubular body 10 can be absorbed or degraded in body tissues in several weeks. By constructed as above, the tubular body 10 can be attached to sclera so that ocular fluid may leave the eye to flow through the conduit 141, thereby lowering ocular pressure.

The tubular body 10 is formed of a bioactive glass material, i.e., capable of being absorbed by the body tissues. Specifically, the tubular body 10 is attracted to the body tissues and tends to be dissolved by the body tissues. Thus, a glaucoma patient may have a minimum feeling of discomfort when the tubular body 10 is attached to sclera. Also, the tubular body 10 may be absorbed by the body tissues as time goes by, thereby forming a tubular, flexible member for healing purposes. As an end, another surgery to remove the tubular body 10 from the sclera is not required.

Referring to FIGS. 9 to 12, a number of implementations of the tubular body 10 are illustrated.

Figure 9:
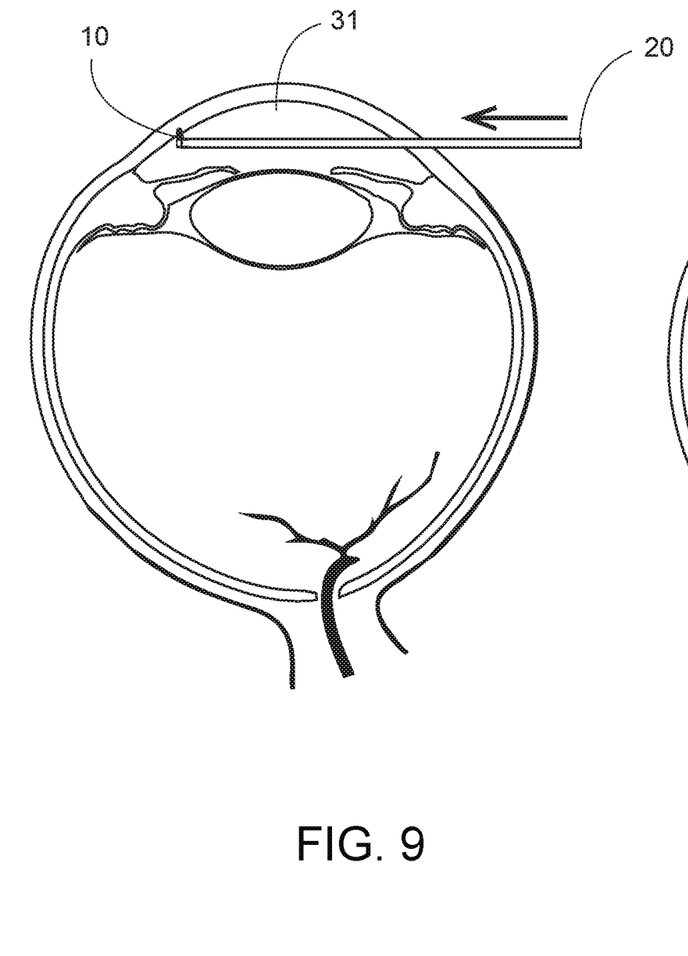
FIG. 9 schematically depicts inserting an implantation device through an anterior section of an eye to attach the tubular body of the first preferred embodiment to sclera.
Figure 10:
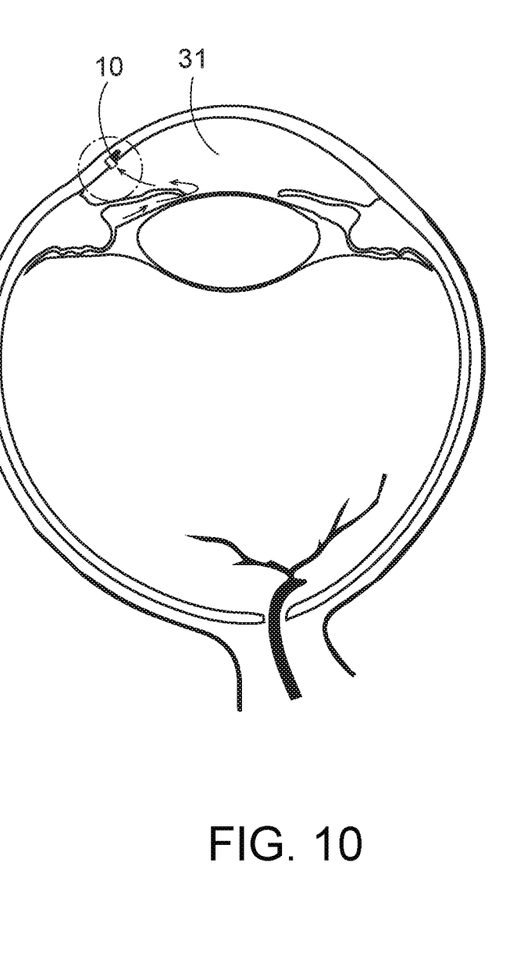
FIG. 10 is a view similar to FIG. 9 showing after the implantation device removal, the tubular body being ready to drain ocular fluid.
Figure 11:
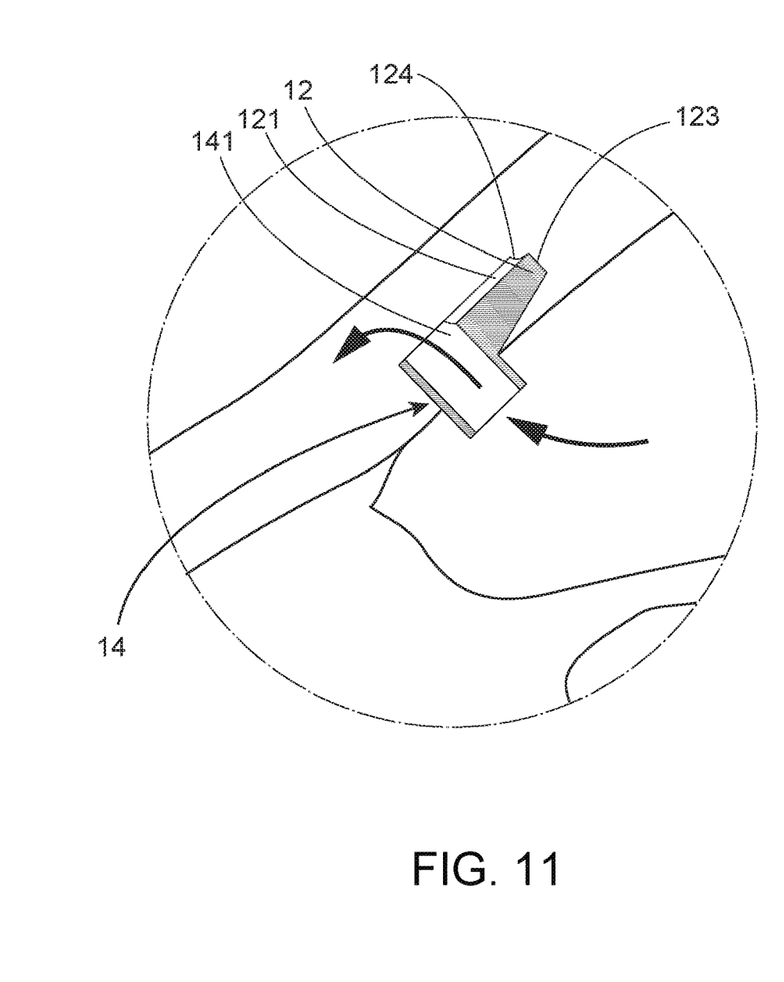
FIG. 11 is a detailed view of the area in a circle of FIG. 10.

As shown in FIGS. 9 to 11 in conjunction with FIGS. 2 to 4A, the tubular body 10 is mounted at an end of an implantation device 20. The implantation device 20 passes through an anterior section 31 of an eye. The sharp end 123 of the implantation member 12 facilitates the tubular body 10 to enter and attach to the sclera. After attaching to the sclera, a medically employee may slightly adjust an angle of the implantation device 20 to attach a maximum portion of the implantation member 12 to the sclera.

In the second preferred embodiment, the implantation member 12 of the tubular body 10 is attached to the sclera, and the conduit 141 communicates with the anterior section 31. Thus, ocular fluid may leave the anterior section 31 through the conduit 141, thereby lowering intraocular pressure.

Figure 12:
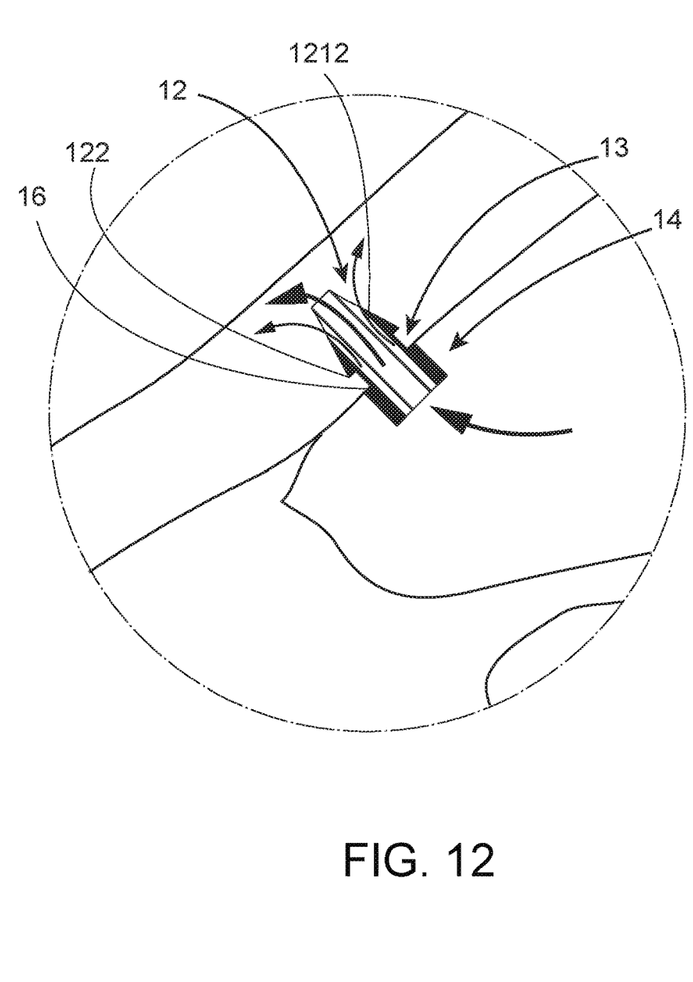
FIG. 12 is a view similar to FIG. 11 showing the tubular body of the third preferred embodiment attached to the sclera and draining ocular fluid.

As shown in FIG. 12 in conjunction with FIGS. 5 to 6A, the implantation member 12 of the tubular body 10 of the third preferred embodiment is attached to the sclera, and the conduit 141 communicates with the anterior section 31.

Thus, ocular fluid may leave the anterior section 31 through the conduit 141 or the tunnels 1212, thereby lowering intraocular pressure.

While the invention has been described in terms of preferred embodiments, those skilled in the art will recognize that the invention can be practiced with modifications within the spirit and scope of the appended claims.

What is claimed is:

1. A shunt for draining ocular fluid, comprising:
   a tubular body formed of a material configured to be absorbed by body tissues, the tubular body including an implantation member, a conduit, and a fluid guide member extending out of the implantation member;
   wherein the implantation member and the conduit are formed integrally;
   wherein the implantation member includes at least one anchor member; and
   wherein the conduit passes through the implantation member and the fluid guide member,
   wherein the fluid guide member is aligned with the implantation member so that the tubular body is shaped as an I in a side elevation, and
   wherein the implantation member includes a tapered anchor member at one end, with a plurality of lengthwise tunnels equally spaced around and separated from the conduit, each tunnel being parallel to the conduit and passing through the tubular body and extending through the fluid guide member and the implantation member,
   wherein each of the plurality of lengthwise tunnels extends through the tubular body and opens at the tapered anchor member of the implantation member.

2. The shunt for draining ocular fluid of claim 1, wherein the tubular body includes a second layer formed of either a material having a composition of silica configured to be absorbed by body tissues over years, or a bio-inert glass material configured to remain in body tissues forever.

3. The shunt for draining ocular fluid of claim 1, further comprising an annular groove disposed between the tapered anchor member and the fluid guide member, and an annular shoulder disposed between the annular groove and the fluid guide member.

4. The shunt for draining ocular fluid of claim 1, wherein the conduit has two open sides.

5. The shunt for draining ocular fluid of claim 1, wherein each of the least one anchor member is substantially half-spherical or tapered.

6. The shunt for draining ocular fluid of claim 1, wherein the conduit has an opening shaped as a circle, an oval, a hexagon, or a polygon.

\* \* \* \* \*